United States Patent [19]

DeLuca et al.

[11] Patent Number: 4,818,542
[45] Date of Patent: Apr. 4, 1989

[54] POROUS MICROSPHERES FOR DRUG DELIVERY AND METHODS FOR MAKING SAME

[75] Inventors: Patrick P. DeLuca, Lexington, Ky.; Motoko Kanke, Fukuyama; Toyomi Sato, Tokyo, both of Japan; Hans G. Schroeder, Encinitas, Calif.

[73] Assignee: The University of Kentucky Research Foundation, Lexington, Ky.

[21] Appl. No.: 846,513

[22] Filed: Mar. 31, 1986

Related U.S. Application Data

[63] Continuation of Ser. No. 551,414, Nov. 14, 1983, abandoned.

[51] Int. Cl.$^4$ .................. A61K 9/16; A61K 9/50; A61K 9/52; B01J 13/02
[52] U.S. Cl. .......................... 424/491; 34/5; 264/4.6; 424/486; 424/492; 424/497; 424/499; 424/501; 424/DIG. 7; 427/213.3; 427/212.31; 427/213.35; 427/213.36; 428/402.24; 514/965
[58] Field of Search .................. 264/4.6; 427/213.3, 427/213.31, 213.35, 213.36; 428/402.24; 424/469, 486, 19, 22, DIG. 7, 491, 492, 497, 499, 501; 34/5

[56] References Cited

U.S. PATENT DOCUMENTS

| 3,460,972 | 8/1969 | Nack ........................... 427/213.3 X |
| 3,737,337 | 6/1973 | Schnoring et al. ......... 427/213.3 X |
| 3,943,063 | 3/1976 | Morishita et al. .............. 427/213.36 |
| 4,384,975 | 5/1983 | Fong .............................. 427/213.36 |

OTHER PUBLICATIONS

Beck et al.: "A New Long-Acting Injectable Microcapsule System . . . ", *Fertility and Sterility*, vol. 31, No. 5, May 1979, pp. 545–551.

Fong et al.: "Evaluation of Biodegradable Microspheres Prepared by a Solvent Evaporation Process . . . ", *J. of Controlled Release*, 3 (1986) 119–130.

*Primary Examiner*—Richard D. Lovering
*Attorney, Agent, or Firm*—Burns, Doane, Swecker & Mathis

[57] ABSTRACT

Controlled release drug delivery systems comprised of spherical microporous polymeric network of interconnecting channels containing pore incorporated drugs or other agents wherein the drugs or agents are confined within the pore channel are described. Also disclosed are processing parameters in connection with the novel method of the invention for obtaining drug delivery systems especially suited for parenteral as well as oral administration.

25 Claims, 14 Drawing Sheets

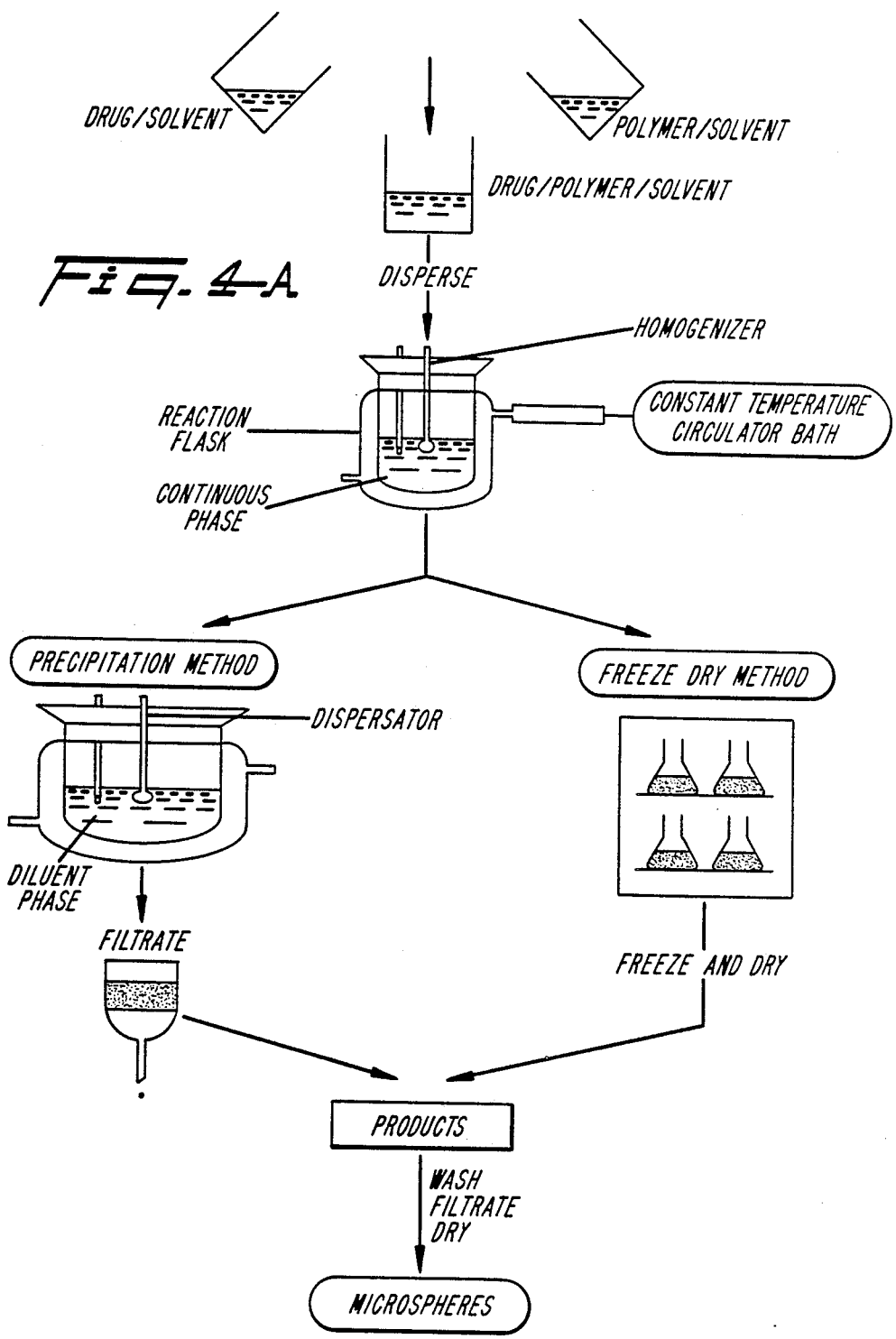

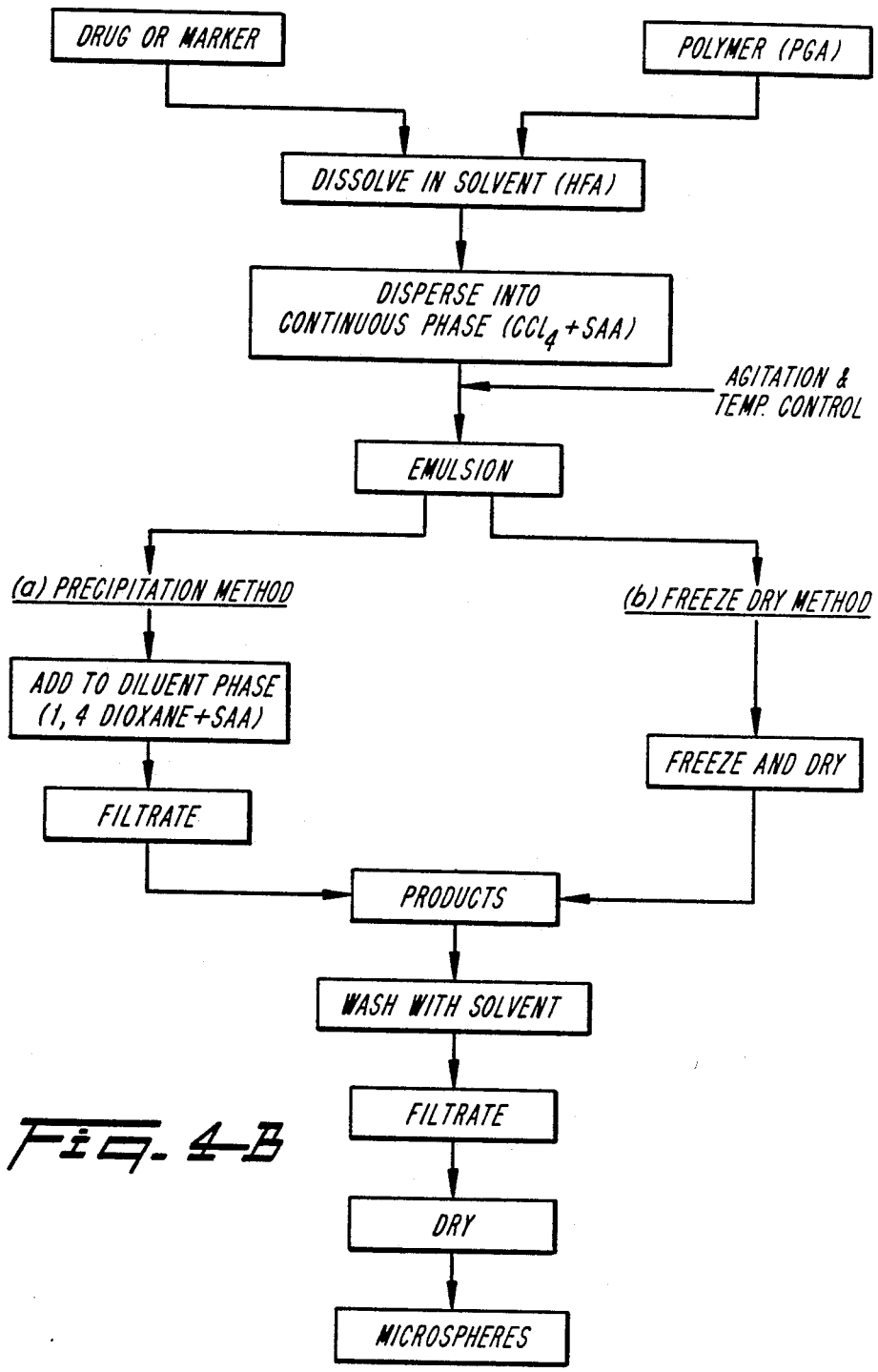
Fig. 4-B

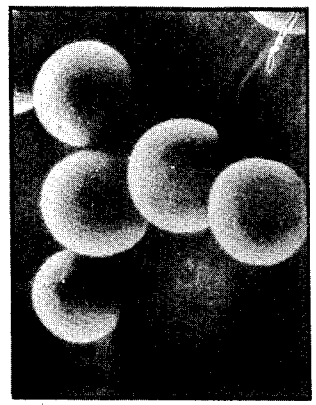 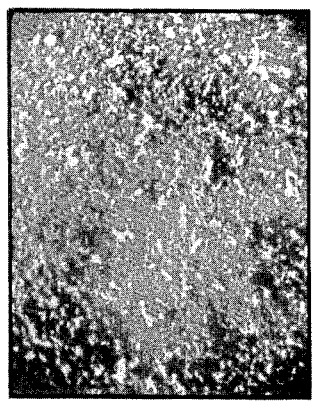
Fig. 5A    Fig. 5B
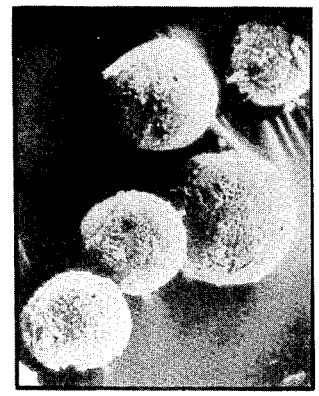 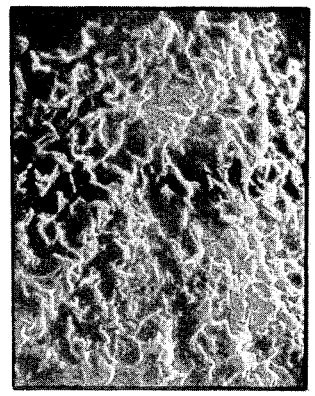
Fig. 6A    Fig. 6B

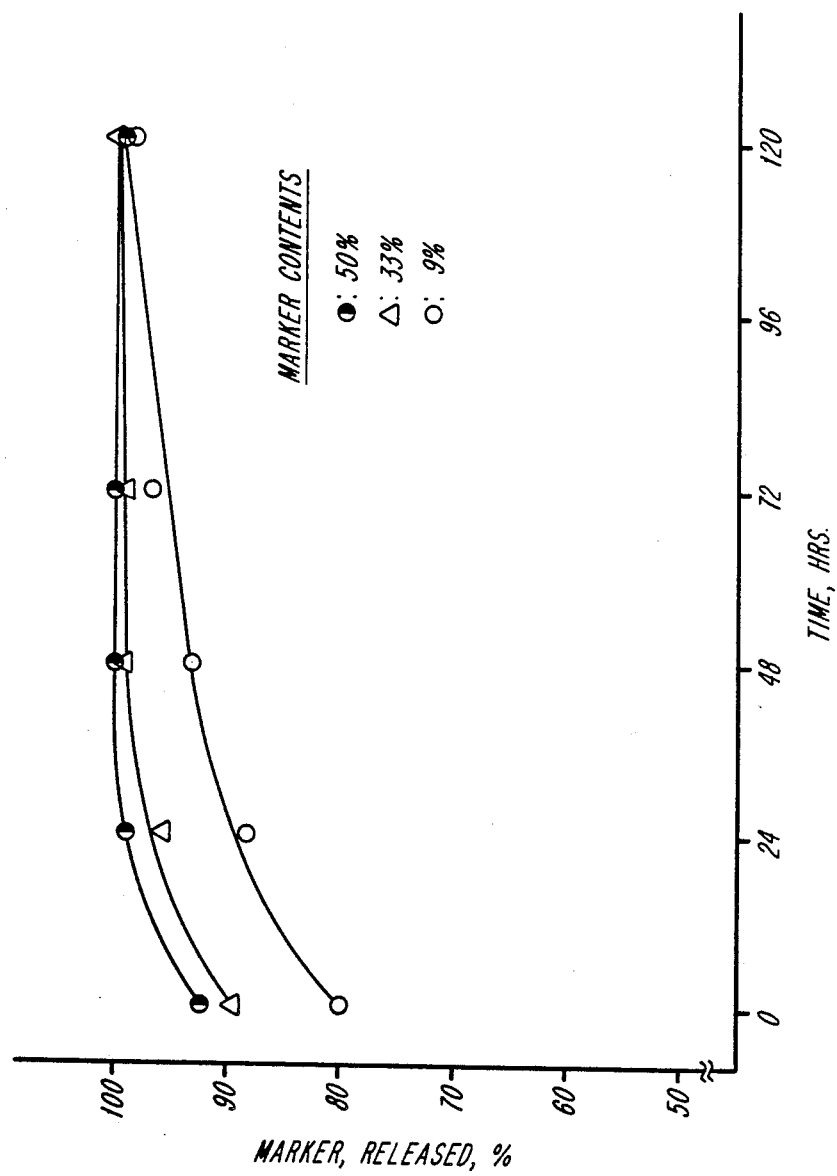

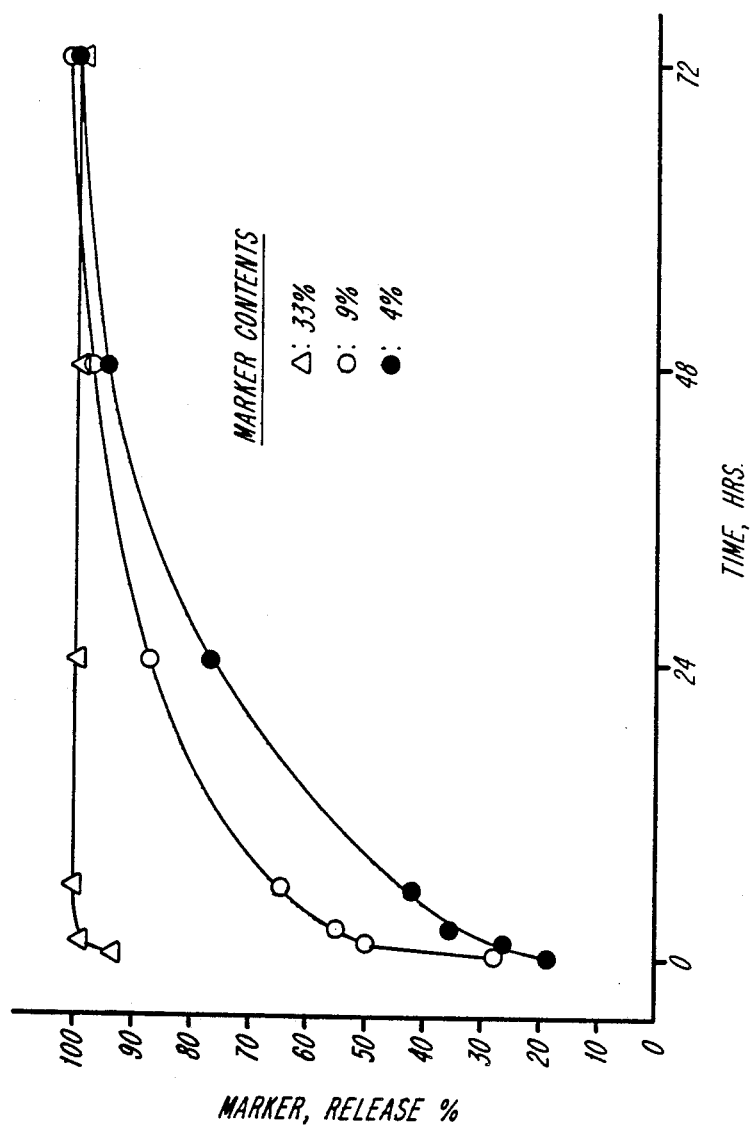

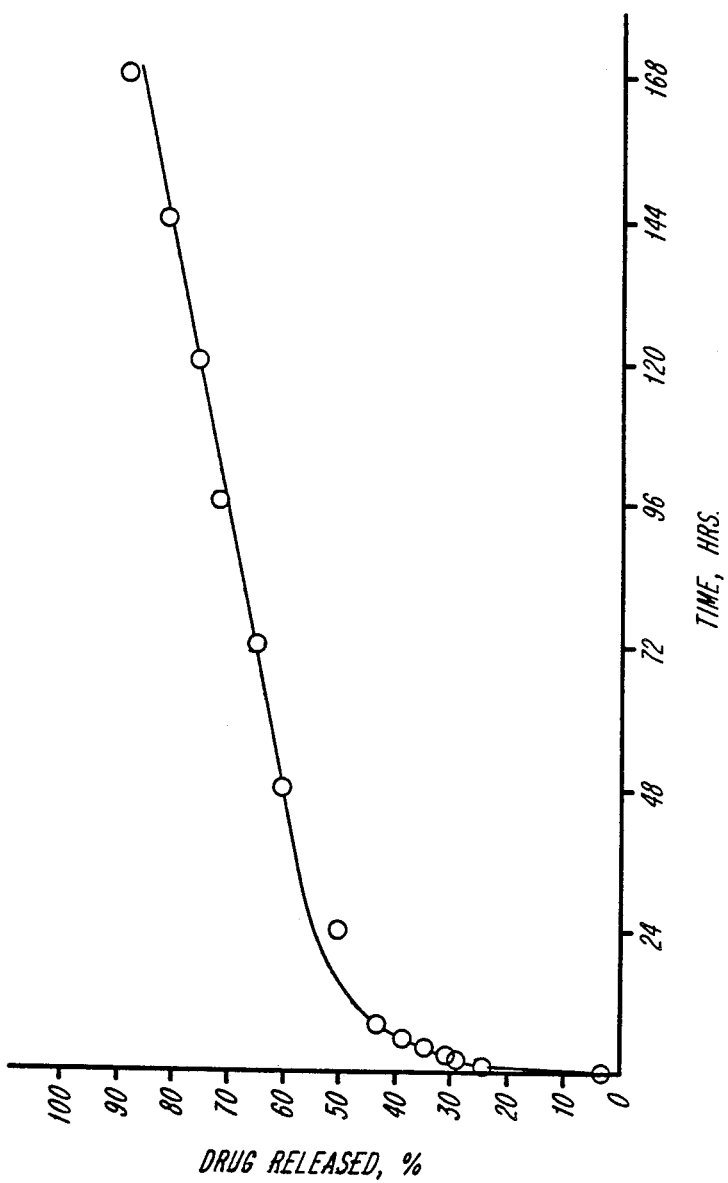

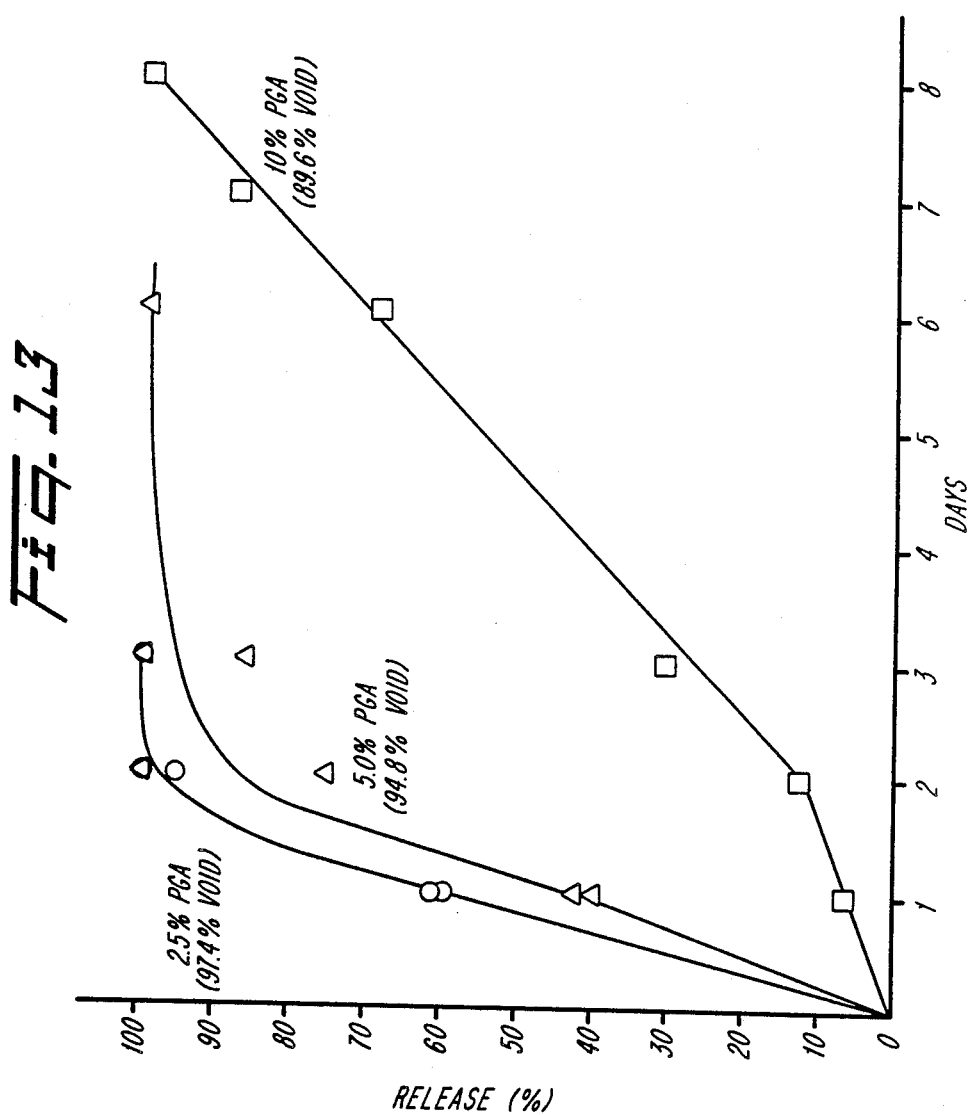

Fig. 14-A
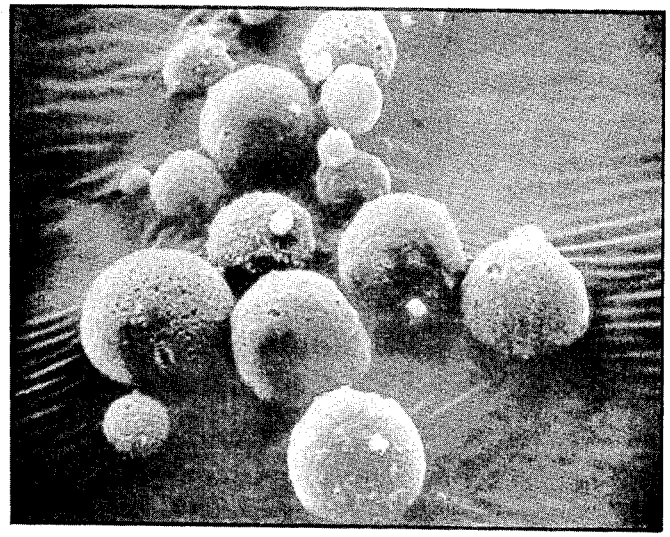
Fig. 14-B
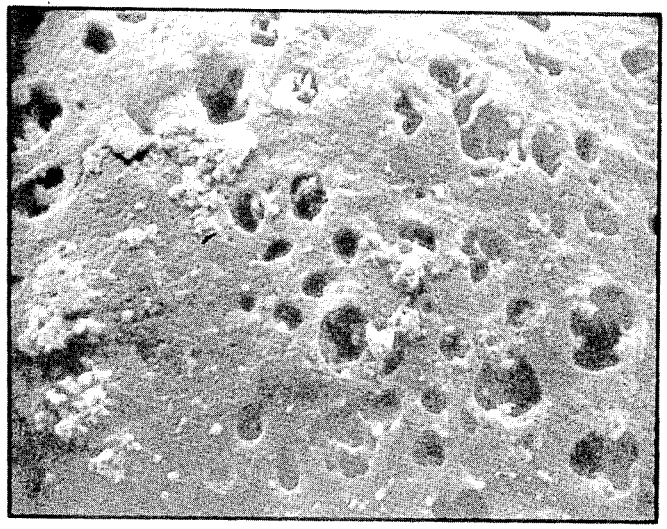

POROUS MICROSPHERES FOR DRUG DELIVERY AND METHODS FOR MAKING SAME

This application is a continuation of application Ser. No. 551,414, filed Nov. 14, 1983, and now abandoned.

BACKGROUND OF THE INVENTION

(1) Field of the Invention

The present invention relates generally to spherical polymer matrices for the controlled release of various drug(s) or other selected agents. More particularly, this invention describes methodology for preparing highly porous spherical polymer matrices with preselected incorporated agents, e.g., therapeutics, dispersed within the confines of the pores therein for controlled delivery to target physiological systems and resulting biodegradable microspheric drug carrier or controlled delivery systems.

(2) State of the Art

A wide variety of microencapsulation drug delivery systems have been developed heretofore for the rate controlled release of therapeutics or other agents. For instance, considerable research has been devoted to incorporating therapeutic agents into polyesters such as poly($\epsilon$-caprolactone), poly($\epsilon$-caprolactone-CO-DL-lactic acid), poly(DL-lactic acid), poly(DL-lactic acid-CO-glycolic acid) and poly$\epsilon$-caprolactone-CO-glycolic acid) in which release was diffusion controlled. See, for example, Pitt, C. G. (Pitt, C. G., Gratzl, M. M., Jeffcoat, A. R., Zweidinger, R., Schindler, A., Sustained Drug Delivery Systems. II. Factors Affecting Release Rates from Poly($\epsilon$-caprolactone) and Related Biodegradable Polyesters. *J. Pharm. Sci.*, 68, 1534 (1979). These systems were fabricated as films and capsules and the results suggest that the devices can be prepared to erode after release of the drug is essentially completed. Degradation of at least the polyesters has been reported to proceed by random hydrolytic cleavage of ester linkages by an autocatalytic process the rate of chain cleavage being influenced by chemical and morphological factors.

Sustained release systems of antimalarial agents and sulfadiazine in glycolic-lactic acid copolymers have also been reported. Wise, D. L., Gesser, J. D., McCormick, G. J., Sustained Release of a Dual Anti-malarial System, *J. Pharm. Pharmacol.*, 31, 201 (1979). Wise, D. L., McCormick, G. J., Willet, G. P., Anderson, L. C., Sustained Release of an Antimalarial Drug Using a Copolymer of Glucolic/Lactic Acid, Life Sci., 19, 867 (1976). Wise, D. L., McCormick, G. J., Willet, G. P., Anderson, L. C., Howes, J. F., *J. Pharm. Pharmacol.*, 30, 686 (1978). Methods reported by the foregoing investigators involved dissolving the agents in a suitable solvent and either spray drying or casting films according to usual methods and evaporating the solvent. Various narcotic antagonists and steroids have been incorporated in films and implanted in rats [e.g., see Woodland, J. H. R., Yolles, S., Blake, D. A., Helrich, M., Meyer, F.J., Long-Acting Delivery Systems for Narcotic Antagonists:I. *J. Med. Chem.*, 16, 897 (1973). Jackanicz, T. M., Nash, H. A., Wise, D. L., Gregory, J. B., Polylactic Acid as a Biodegradable Carrier for Contraceptive Steroids, *Contraception*, 8, 227 (1973). Anderson, L. C., Wise, D. L., Howes, J. F., An Injectable Sustained Release Fertility Control System, *Contraception*, 13, 375 (1976)] and incorporated into particles injected subcutaneously [Yolles, S., Time-Release Depot for Anticancer Drugs: Release of Drugs Covalently Bonded to Polymers, *J. Parent, Drug Assoc.*, 32, 188 (1978)]. The release of a number of anti-tumor agents has been evaluated in implantable systems as reported in [Yolles, S., Time-Release Depot for Anticancer Drugs: Release of Drugs Covalently Bonded to Polymers, *J. Parent, Drug Assoc.*, 32, 188 (1978)], and the antibiotic Mitomycin C has been encapsulated in microspherical carriers of gelatin and administered intraveneously [Yoshioka, T., Hashida, M., Muranishi, S., and Sezaki, H., Specific Delivery of Mitomycin C to Liver, Spleen and Lung: Nano-and Microspherical Carriers of Gelatin. *Intern J. Pharm.*, 81, 131 (1981)]and the effect of size on in vivo distribution and the potential for antibiotic targeting discussed. The size distribution of the microspheres (i.e. 5–30 $\mu$m) reported in the last mentioned publication was very broad, especially for intravenous administration. Recently the in-vitro release of local anesthetics from polylactic acid spheres prepared by a solvent evaporation process has, likewise, been reported [Wakiyama, N., Kaxuhiko, J., Nakano, M., Influence of Physicochemical Properties of Polylactic Acid on the Characteristics and In Vitro Release Patterns of Polylactic Acid Microspheres Containing Local Anesthetics, *Chem. Pharm. Bull.*, 30, 2621 (1982)]. The patterns of release from these polylactic acid spheres were characterized by the various degrees of degradation of the polymer as well as solubilities of loaded drugs although no attempt was apparently made to evaluate this parameter. Additionally, it is apparent that the solubility of the drug played an important role in the rate and extent of release. Scanning electron photomicrographs also revealed varying degrees of erosion and deformation of the spheres after release.

It will be seen from the foregoing that while the controlled release delivery of pharmaceuticals or other agents from heretofore described polymeric systems has been principally limited to oral, topical or implantable systems in which the considerations relative to pore size and/or cell size within the carrier matrix as well as the overall dimensions of the microspheres to be administered along with the rate of release and the relative absorption rate from a bioavailability standpoint are distinctly different from the evaluation parameters involved in the utilization of these microsphere delivery systems for parenteral, i.e., intravenous, intraarterial, intraocular or inhalation administration routes to which the present invention is particularly applicable.

SUMMARY OF THE INVENTION

It is, therefore, a primary object of the present invention to afford novel porous microspheres for the controlled delivery of drugs or other matrix confined materials to target organs or systems in warm-blooded animals in need thereof and to methods for making such microspheres.

A further object of the present invention is to provide methods for preparing porous microspheres of heretofore unattainable narrow-range size distribution particularly suitable for use as parenterally administerable drug delivery systems for injectable and inhalation dosage forms as well as facilitating sustained drug release via more conventional oral administration routes.

It is a still further object of the present invention to provide porous microsphere matrices wherein the accessability of the drug or other incorporated agent is not dependent upon the physical or chemical erosion of the polymer for release.

Another object of the present invention is to provide chemically modified polymer compositions suitable for use in the spherical polymer matrices of the invention whereby porosity as well as degradation of the polymer substrate after release of the matrix confined agent for release can be predetermined and controlled.

A still further object of the present invention is to provide porous polymeric microspheric drug delivery systems which allow targeting of drugs or other agents to specific host tissues or cells via injection or inhalation providing high localized concentrations, sustained activity, systemic administration and treatment not possible by other methods thereby minimizing undesirable systemic effects of toxic drugs administered directly into the circulation.

These and other similar objects, advantages and features are accomplished according to the methods, products and compositions of the present invention.

BRIEF DESCRIPTION OF DRAWINGS

FIGS. 4A and 4B generally depict the preparative methods of the present invention.

FIGS. 5A and 5B depicts the shape and surface appearance of polyglycolic (PGA) microspheres prepared by Dilution-Prescription Method.

FIGS. 6A and 6B depicts the shape and surface appearance of PGA microspheres prepared by Freeze Dry Method.

FIG. 7 is a graph of the release profile from matrices which were prepared by Precipitation Method and contain different amounts of marker.

FIG. 8 is a graph of the release profile form matrices which were prepared by Freeze Dry Method and contain different amounts of marker.

FIG. 9 is a graph of the release profile from matrices which were prepared by Freeze Dry Method and contain prednisolone acetate.

FIG. 13 is a graph of the release of dye from polymer in plasma.

FIGS. 14A and 14B depict PGL microspheres containing blue dye manufactured by Dilution-Prescipitation Method.

DESCRIPTION OF THE PREFERRED EMBODIMENTS

Figure 1A:
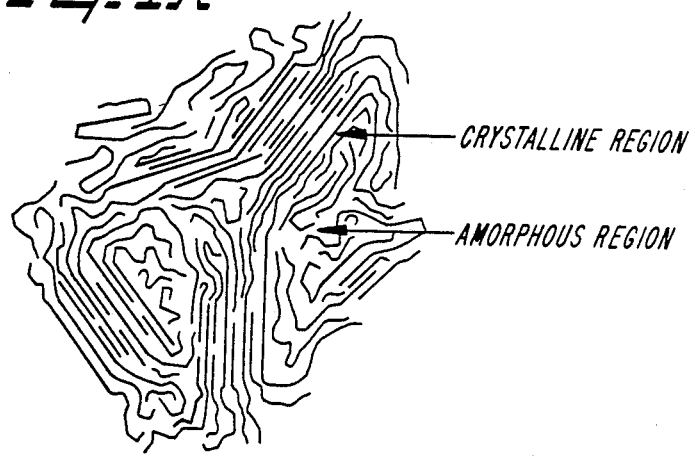
FIG. 1 is a drawing of a polymer with a low degree of crystallinity in accordance with the practice of the present invention and a drawing of a polymer with a high degree of crystallinity.

The porous polymeric microspheres of the present invention are derived from copolymeric and homopolymeric polyesters containing hydrolyzable ester linkages which are, therefore, bidoegradable. Typically preferred of such polyesters are polyglycolic (PGA) and polylactic (PLA) acids, and copolymers of glycolide and L(-lactide) (PGL). The aforementioned polyesters are particularly suited for the methods and compositions of the present invention by reason of their characteristically low human toxicity and virtually complete biodegradability. Of course, it will be understood that the particular polyester or other polymer, oligomer, copolymer, etc., utilized as the microspheric polymer matrix is not critical and a variety of polymers may be utilized as a consequence of the novel processing methods of the invention which yield the desired microspheres of the porosity, consistency, shape and size distribution essentially irrespective of the source of polymer utilized. Accordingly, other biodegradable or bioerodable polymers or copolymers evidencing the necessary low degree of toxicity suitable for use in the present invention include, for example, gelatin, agar, starch, arabinogalactan, albumin, collagen, natural and synthetic materials or polymers, such as, poly($\epsilon$-caprolactone), poly($\epsilon$-caprolactone-CO-lactic acid), poly($\epsilon$-caprolactone-CO-glycolic acid), poly($\beta$-hydroxy butyric acid), polyethylene oxide, polyethylene, poly(alkyl-2-cyanoacrylate), (e.g., methyl, ethyl, butyl, etc.), hydrogels such as poly(hydroxyethyl methacrylate), polyamides (e.g., polyacrylamide), poly(amino acids) (i.e., L-leucine, L-aspartic acid, $\beta$-methyl-L-aspartate, $\beta$-benzyl-L-aspartate, glutamic acid and the like), poly(2-hydroxyethyl DL-aspartamide), poly(ester urea), poly(L-phenylalanine/ethylene glycol/1,6-diisocyanatohexane) and poly(methyl methacrylate).

The foregoing exemplary natural and synthetic polymers suitable for use in the present invention are, of course, either readily available commercially or are obtainable by condensation polymerization reactions from the suitable monomers or, comonomers or oligomers. For instance, homopolymers and copolymers of glycolic and lactic acids can be prepared by direct polycondensation or by reacting glycolide and lactide monomers as disclosed by Gilding, D. K., Reed, A. M., Biodegradable Polymers for Use in Surgery - Polyglycolic/Poly(lactic acid) Homo- and Copolymers: 1, Polymer, 20, 1459 (1979). Structurally, polyglycolic acid (PGA) has the following structure:

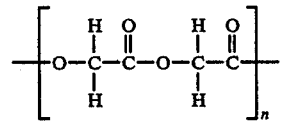

whereas the related copolymer polyglycolic acid/-polylactic acid (PGI; has the structure depicted below:

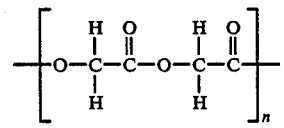

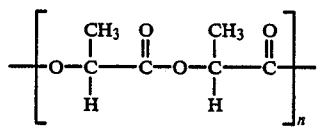

Both of the foregoing are polyester type polymers which readily degrade via hydrolysis at the ester linkages and by appropriately selecting suitable molecular weight polyesters, modifying the degree of cross-linking and the degree of crystallinity, the biodegradation properties of such polymers may be advantageously controlled. As pointed out previously, however, in accordance with the present invention the necessity for biodegradation or bioerosion of the polymer matrix for release of the agent incorporated therein to occur is obviated by reason of the intrinsic porosity characteristics of the polymer matrices of the invention and the fact that the incorporated agent or agents are matrix confined within the interconnecting channels or pores of the spherical polymer. However, in accordance with alternative and preferred embodiments of the present invention the possibility that the matrix could be coated with a film or cross-linking agent to inhibit or control release, thereby allowing bioerosion to influence release is not in any way precluded and may, in fact, depending upon the nature of the incorporated agent as well as the rate of release required in the target organ system may be desirable or advantageous. For example, in those instances where it may be desirable to inhibit or retard drug release rates, more extensive cross-linking of the copolymer or polymer may be achieved by the addition of higher concentrations of suitable cross-linking agents such as glyoxal, succinaldehyde, glutaraldehyde, 3-methylglutaraldehyde, methyleneacrylamide, bisacrylamide and similar cross-linking agents. Likewise, the reduction or elimination of crosslinks in the copolymers or polymers of the invention will result in enhanced biodegradability. On the basis of such polymer modifications, it is evident that the release of the incorporated agent or agents will be essentially complete, i.e., 90% before any erosion or degradation of the polymer matrix occurs, and, thus, the polymer composition can be preselected to permit controlled clearance from the target system after release of the incorporated drug.

Figure 1B:
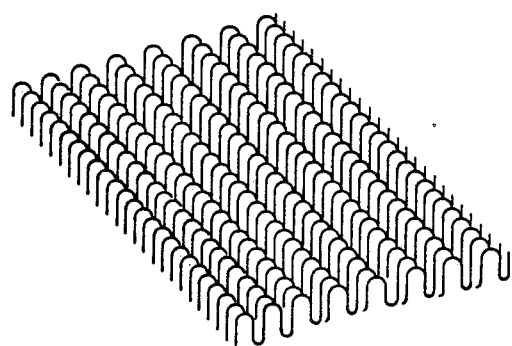
Figure 2:
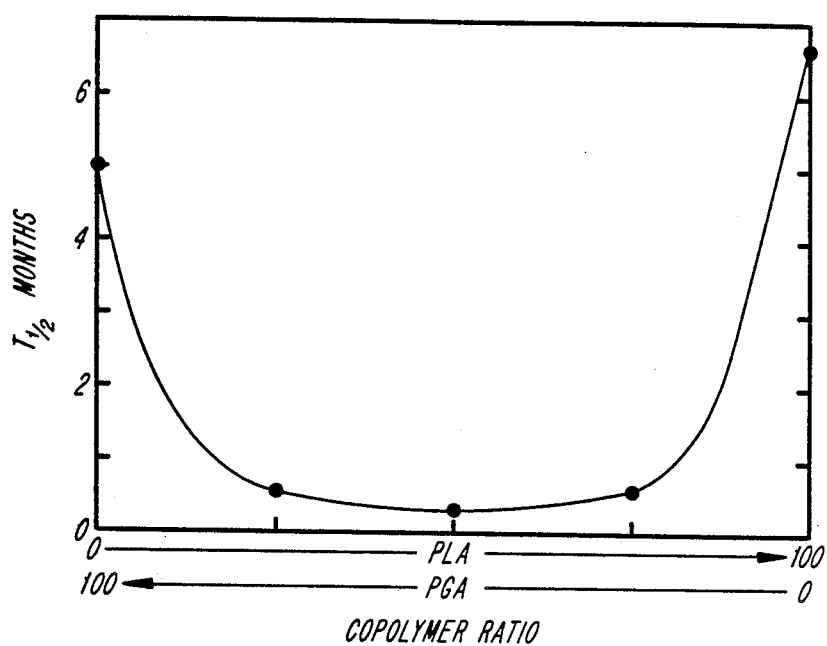
FIG. 2 is a graph of half-life in months versus various ratios of polyglycolic (PGA) and polylactic (PLA) as copolymer implanted in rat tissues.
Figure 3:
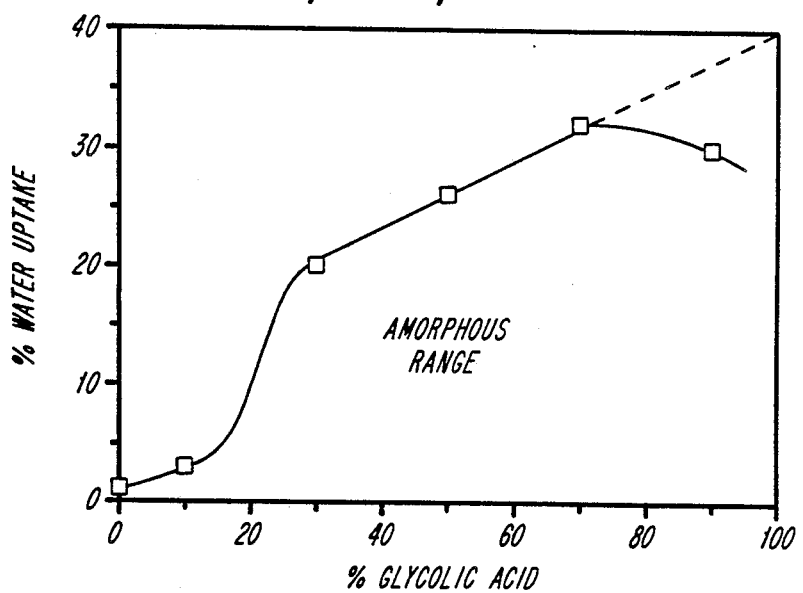
FIG. 3 is graph of percent water uptake versus percent glycolic acid for glycolide/lactide copolymers.

The polymers utilized in accordance with the invention exist in the crystalline form with amorphous regions interdispersed between the crystalline areas as shown, for example, in FIG. 1. Hydrolysis rates have been shown to be higher in the amorphous regions. For the copolymers of PLA/PGA, the degree of crystallinity is reduced at a composition of equal amounts of PLA and PGA. As shown in FIG. 2, the half-life for the degradation of polymer in rat tissue was lowest at a 50-50 composition. FIG. 3 shows that the water uptake is highest in this range which constitutes the amorphous region. Therefore bioerosion occurs in the amorphous regions initially and eventually the backbone is destroyed and the matrix will collapse, thereby accelerating the bioerosion and elimination of the polymer.

Consistent with the controlled conditions of the methods of the present invention, spherical polymer matrices or microspheres having a diameter range between about 1 to 150 microns ($\mu$m) can be prepared in narrow size ranges for targeting to various organ or organ systems via parenteral injection or inhalation. A more preferred range for the spherical polymer matrices of microspheres is between about 0.5 to 50 microns. The integratable methods for preparing porous spherical matrices consistent with the present invention result in microspheres in which essentially all of the agent(s) incorporated within the pores of the drug delivery system is readily available for release. Essentially the foregoing principle objective of the invention is accomplished by forming emulsified droplets or spheres consisting of a homogeneous mixture of polymer (or copolymer), solvent and matrix incorporated agent from a solution of a preselected polymer and agent dispersed in a continuous (non-solvent phase). Removal of the solvent from the sphere by any one or combination of (1) freeze drying, or (2) dilution-precipitation extraction, creates the interconnecting network of pores wherein the incorporated agent is confined within the walls and channels of the pores as opposed to random distribution within the more poorly defined interstices of the polymer. As used in the specification and claims, the expression "pore incorporated agent" is used to define the relative specific location of the agent confined essentially completely inside the pores of the porous microspheres of the invention. Similarly, the term "agent" specifically encompasses any diagnostic or pharmacologically active material which would be generally classifiable as a drug suitable for introduction into a human or other warmblooded animal host, as well as other materials or compositions including, for instance, dyes, antigens, antibodies, enzymes, flavors, comestibles and the like and mixtures thereof.

The drug delivery systems in accordance with the present invention are ideally suited for administration by parenteral or inhalation routes. It will be appreciated by those skilled in the art that the porous microspheres of the present invention containing pore incorporated drugs for release to target cells or tissues, therefore, may be administered alone or in admixture with appropriate pharmaceutical diluents, carriers, excipients or adjuvants suitably selected with respect to the intended route of administration and conventional pharmaceutical practices. For example, for parenteral injection, dosage unit forms may be utilized to accomplish intravenous, intramuscular or subcutaneous administration, and for such parenteral administration, suitable sterile aqueous or non-aqueous solutions or suspensions, optionally containing appropriate solutes to effectuate isotonicity, will be employed. Likewise for inhalation dosage unit forms, for administration through the mucus membranes of the nose and throat or bronchiopulmonary tissues, suitable aerosol or spray inhalation compositions and devices will be utilized.

Consistent with other preferred embodiments of the present invention, the porous microspheric drug delivery systems of the invention may be additionally coated or modified to advantageously influence the targeting of the release of the incorporated drug therein to preselected target cells, tissues or organs. For example, the drug delivery microspheres may be coated with various agents, e.g., proteins, surfactants, antibodies or receptor site specific drugs which may be the same or different from those incorporated in the porous microsphere whereby the release of the incorporated drug is concentrated at the targeted system.

The preparative methods of the present invention are generally depicted in FIGS. 4A and 4B.

In accordance with the methods for making the porous microspheres of the invention, the desired polymer or copolymer and the drug(s) or other agent(s) are dissolved separately in a suitable solvent. The polymer and drug solutions are mixed together in the appropriate manner to provide a polymer concentration ranging between about 2.5 to 18% w/w and a drug:polymer ratio ranging between about 1:1 to 1:10. The temperature of the resultant solution is controlled between about 30°-45° C. The drug-polymer solution comprising the dispersed phase is dispersed into the continuous phase containing an appropriate surface active agent at a thermostatically controlled temperature generally in the range of 10°-20° C. The foregoing is accomplished by forcing the dispersed phase under pressure through a fine orifice nozzle. The continuous phase which is 10–20 times by weight of the dispersed phase is then agitated by a dispersator. Following the introduction of the dispersed phase, one of two recovery methods (see FIG. 4) is utilized to stabilize and recover the drug-loaded microspheres for final processing.

More specifically, consistent with the freeze-dry method of the invention, following dispersion, the temperature is maintained at 10°-20° C., preferably 15° C., for two minutes then increased to 45°-55° C., preferably 50° C., over a three minute period. Vigorous agitation of the mixture is continued during this period. When the temperature reaches 50° C., either a refrigerant solution is circulated through the jacket from the bath or the container is immersed in dry ice-methanol and cooled to a temperature which will freeze the drug-polymer-solvent phase and not the continuous phase. The suspension or emulsion (solid dispersion phase in liquid continuous phase) is quickly transferred to precooled vials ($-40°$ to $-60°$ C.) and cooled to $-40°$ to $-60°$ C. in a freeze dryer, freezer or dry ice-acetone bath. The solvent in the suspended droplets (microspheres) and the continuous phase solvent are removed by freeze drying. Upon completion of the freeze dry cycle the microspheres are washed with a suitable solvent, filtered and air dried.

In the dilution-precipitation method of the invention, following dispersion, the temperature is maintained at 10°-20° C., preferably 15° C., for two minutes, then increased to 45°-55° C., preferably 50° C., over a three minute period. The dispersion is then transferred to a vessel containing a diluent solvent at room temperature as depicted in FIG. 4. Agitation is continued for 30 minutes using a vibromixer. During the process the dispersed phase solvent is removed from the drug-polymer-solvent emulsion droplets by extraction causing solidification of the droplets. The solid spheres are then removed by filtration, washed with a suitable solvent and air dried.

Solvents for the dispersed phase and the continuous phase will of course differ in order to attain phase separation and, are therefore, selected based upon the solvent requirements for each phase. More particularly, the solvent for the dispersed phase should dissolve the polymer and the incorporated agent and remain in the emulsified droplets with the drug and polymer in the continuous phase until leached out by a diluent solvent or removed by vaporization or evaporation. In this way pores are formed in the drug-polymer matrix. In the case of PGA polymer into which water soluble markers or agents are incorporated, hexafluoroacetone sesquihydrate (HFA) is an appropriate solvent. Other solvents which can be used, depending upon characteristics of polymer and incorporated agents, include water, hexafluoroisopropanol (HFIP), methylene chloride, tetrahydrofuran, hexane, benzene. Solvents for the continuous phase should not dissolve the polymer and should emulsify the dispersed phase. Solvents include benzene, dioxane, acetone, methylene chloride, chloroform, carbon tetrachloride, toluene, ethyl alcohol, acetonitrile, p-xylene, tetrahydrofuran and mixtures of these solvents.

A diluent (non-solvent) phase can also be employed to dilute the continuous phase following dispersion of the polymer:agent solution. The diluent should be miscible with the continuous phase and dispersed phase solvents but not dissolve the polymer or incorporated agent. Examples of solvents include 1,4-dioxane, cyclohexanone, acetone, ethanol, acetonitrile, dimethylformamide, tetrahydrofuran and cyclohexanol.

The concentration of polymer in the dispersed phase directly influences the porosity or "void" space in the final microsphere product as well as the shape of the microsphere. A concentration of 2.5% to 10% w/w polymer yields dimensionally suitable spherical particles. With respect to the concentration of the pore incorporated agent, up to 50% by weight of the polymer has been achieved with consistent results.

In accordance with another preferred embodiment of the present invention, hydrophilic colloids are employed to improve the yield and prevent phase inversion in the continuous and diluent phases. Substances which can be utilized in concentrations ranging between about 0.5 to 5% include anionic surfactants such as sorbitan, gelatin and gelatin derivatives, polyvinyl alcohol, polystyrene sulfonate, hydroxyethylcellulose, hydroxypropylcellulose and related colloids with suitable hydrophilicity.

It has been determined that certain processing parameters influence the recovery methods as well as the resultant microspheres of the present invention. Identifiable parameters include the concentration of polymer in the dispersed phase, the temperature of the dispersed phase at the time of dispersion, the concentration of surfactants in the dispersed phase as well as the ratio of incorporated agent to polymer in the dispersed phase. It will be appreciated that the concentrations, temperatures and ratios referred to hereinabove and in the Examples set forth operable ranges and that other numerical expressions may apply as different solvents, polymers, incorporated agents, etc. are selected.

The shape and surface appearance of microspheres prepared in accordance with the recovery methods of the invention were assessed by Scanning Electron Microscopy (SEM), FIGS. 5–7 as well as by optical micrography.

Figure 10:
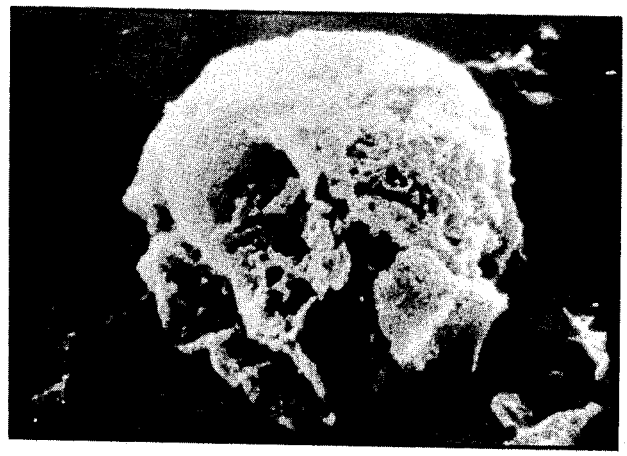
FIG. 10 depicts scanning electron micrography (SEM) micrographs of the PGA matrix manufactured by Freeze Dry Method 72 hours following drug release.
Figure 11:
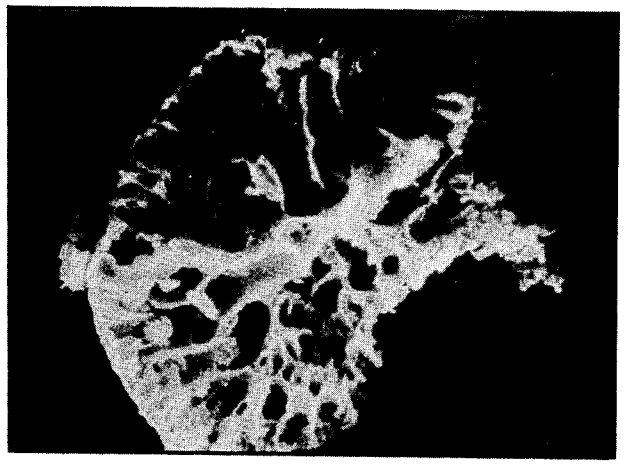
FIG. 11 depicts SEM micrographs of the PGA matrix manufactured by Freeze Dry Method after 120 hours following drug release.
Figure 12:
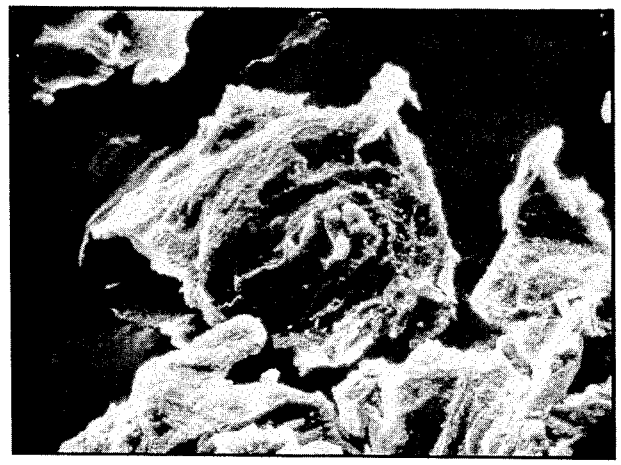
FIG. 12 depicts SEM micrographs of the PGA matrix manufactured by Freeze Dry Method 168 hours following drug release.

Typical release profiles are also shown in FIGS. 7–9. The very water soluble FD&C dye Blue #1 releases within 1-3 days depending upon the concentration of dye (i.e., marker). In all instances release is completed before discernible degradation or erosion of the matrix occurs. FIGS. 10 and 11 show SEM micrographs of the spheres following 72 hours and 120 hours, respectively, in the dissolution media. The spheres were essentially intact indicating minimal erosion. The release of a less-soluble compound, prednisolone acetate is shown in FIG. 9. Essentially 90% of the drug was released after 7 days and degradation of the matrix was very evident after 7 days as shown by the fragmentation in FIG. 12.

The following non-limiting Examples are afforded in order that those skilled in the art may more readily understand the present invention and specific preferred embodiments thereof with respect to the methods and compositions in accordance with the foregoing description.

EXAMPLE 1

FD&C Blue #1 - PGA microspheres (freeze dry recovery)

1. 0.1 g of FD&C Blue #1 was dissolved in 9.9 g of HFA to make a 1% (w/w) solution.
2. 1.0 g of PGA was dissolved in 9.0 g of HFA to make a 10% (w/w) solution.
3. Equal weights of the above are mixed together to form the dispersed phase. The resultant spheres from this combination are very porous having 94.5% "void" space and a dye-polymer ratio of 1:10. In this example 2.0 g of each solution were mixed together and maintained at 37° C. The spherical microporous polymeric network has a degree of porosity of between about 80 to 98 percent as determined by relative void space in relation to the starting concentration of the polymer.

| Dispersed Phase Concentrations: | | |
|---|---|---|
| DYE | POLYMER | SOLVENT |
| 20 mg | 200 mg | 3780 mg |
| 0.5% | 5.0% | 94.5% |

4. The continuous phase constituted 160 g of CCl$_4$ containing 0.1% sorbitan sesquioleate (SO-15) which was maintained at 15° C. in a 500 ml jacketed vessel. A dispersator was located at the center of the vessel for mixing.
5. The dye-polymer-solvent solution was then dispersed via pressure through a fine orifice into the continuous phase which was agitated vigorously with the dispersator. The temperature was maintained at 15° C. and the mixing continued for 2 minutes. The temperature was then increased to 50° C. over a 3 minute period by either circulating 70° C. water through the jacket (or immersing the vessel in a 70° C. water bath).
6. When the temperature reached 50°, a refrigerant solution at −22° C. was circulated through the jacket to freeze the dispersed phase and not the continuous phase (f.p. of CCl$_4$=−22.6°).
7. The above suspension was quickly transferred to pre-cooled (ca −45° C.) 50 ml vials and cooled to −40° to −50° on the shelves in a freeze dryer which had been precooled to −50° C.
8. The suspension was maintained at −50° for 1 hour. Vacuum was applied and the shelves heated to −10° C. and maintained at this temperature for 24 hours to remove the CCl$_4$. The temperature of shelves was increased to 20° C. for 24 hours to remove the HFA. The temperature of the shelves was increased to 35° and maintained for 2 hours to ensure removal of all solvent.
9. The vials containing the spheres were removed from the chamber and stoppered pending washing and evaluation.

EXAMPLE 2

Prednisolone acetate—PGA microspheres (freeze dry recovery)

0.1 g of predonisolone acetate was dissolved in 9.9 g of HFA to make a 1% w/w solution.
1.0 g of PGA was dissolved in 9.0 g of HFA to make a 10% w/w solution.
2.0 g of each solution were mixed together and maintained at 37° C.

| Dispersed Phase Concentrations: | | |
|---|---|---|
| DRUG | POLYMER | SOLVENT |
| 20 mg | 200 mg | 3780 mg |
| 0.5% | 5.0% | 94.5% |

4-9. Steps four through nine were the same as in Example 1.

Spheres obtained by the freeze dry were washed twice with 125 ml volumes of acetone and collected on 0.8, 10, & 50 μm filters. The spheres obtained by the precipitation method were washed with acetone in the size ranges previously obtained by filtration and collected on 0.8, 10, & 50 μm filters. Washing removes approximately 8.5% of the dye or drug from the sphere.

EXAMPLE 3

Characterization of Microporous Microspheres and Release of Model Compounds

SEM Photomicrographs of Examples, 1, and 2 are shown in FIGS. 5–7 at 10-fold differences in magnification. The porous nature is evident from the topography of the magnified surfaces of both methods of preparation.

In-vitro release from the microspheres was determined in 0.1M phosphate buffer (pH 7.4). The spheres were quantitatively transferred to a 15 ml cuvette tube with a screw cap and the buffer added. The tubes were placed on a rocker-type shaker in an oven at 37° C. The tubes were centrifuged at various times and solution samples were removed for spectrophotometric analysis at 630 nm for FD&C Blue #1 and at 245 nm for prednisolone acetate. Release profiles are shown in FIGS. 7–9 for Examples 1 and 2 along with the profiles of other compositions. The release of water soluble dye was essentially complete in 2 to 3 days with spheres prepared by the precipitation and freeze dry methods while the less-soluble prednisolone acetate releases much more slowly, 90% in 7 days.

In experiments at a fixed level of dye, i.e., 4% (by weight of polymer) and variable polymer concentration in the dispersed phase (2.5%, 5% & 10%), the release rate was reduced in relation to the polymer concentration (FIG. 13). The "void" space or the porosity is controlled by the polymer (or solvent) concentration of the dispersed phase.

EXAMPLE 4

FD&C Blue #1 - PGL microspheres
(Dilution-Precipitation Recovery)

1. 0.1 g of FD&C Blue #1 was dissolved in 9.9 g of HFA to make a 1% (w/w) solution.
2. 0.5 g of polygalactin 910 (Vicryl$^R$) was dissolved in 4.5 g of HFA to make a 10% (w/w) solution.
3. Equal weights of the above were mixed together to form the dispersed phase and maintained at 37° C.

| Dispersed Phase Concentrations: | | |
|---|---|---|
| DYE | POLYMER | SOLVENT |
| 20 mg | 200 mg | 3780 mg |
| 0.5% | 5.0% | 94.5% |

The resultant spheres from this combination ratio will be very porous having 94.5% "void" space and a dye-polymer ratio of 1:10.

4–5. Steps four and five are the same as in Example 1.

6. 200 g of 1,4-dioxane (non-solvent diluent) containing 0.1% SO-15 was added to a one-liter vessel and agitated with a vibro-mixer at room temperature.

7. The emulsified Dye-PGA-HFA system in CCl₄ was transferred after reaching 50° C. to the diluent phase and agitation continued for 30 minutes.

8. The suspension was then filtered through a series of filters to collect the spheres in various size ranges of 50 μm, 10–50 μm and 10 μm. See FIGS. 14A and 14B for topography of the microspheres.

EXAMPLE 5

FD&C Blue #1 - Gelatin microspheres
(Dilution-Precipitation Recovery)

0.1 g of FD&C Blue #1 was dissolved in 10.0 g of 10% w/w aqueous gelatin solution. 3.0 g of this mixture was maintained at 37° C. as a dispersed phase.

| Dispersed Phase Concentrations: | | |
|---|---|---|
| DYE | POLYMER | SOLVENT |
| 30 mg | 300 mg | 2670 mg |
| 1.0% | 10.0% | 89.0% |

2. The continuous phase constituted 120 g of CCl₄ containing 2% SO-15 which was maintained at 40° in a 500 ml jacketed vessel. A dispersator was located at the center of the vessel for mixing.

3. 0 g of the dye-gelatin-water solution was dispersed via pressure through a fine orifice into the continuous phase which was agitated vigorously. The temp. was maintained at 40° C. and the mixing continued for 3 min.

4. 100 g of 1,4-dioxane containing 2% SO-15 was added slowly to the emulsified dye-gelatin-water system in CCl₄ to harden the gelatin matrix and agitation continued for 30 minutes.

5. A refrigerant solution was circulated through the jacket and the system cooled to 14°.

6. 50 g of a curing solution, consisting of 10 g of 50% glutaraldehyde and 40 g of 1,4-dioxane containing 2% SO-15, was added dropwise (4 ml/min) to the dye-gelatin-water system in CCl₄. Agitation continued at 14° C. for 30–60 minutes.

Figure 15A:
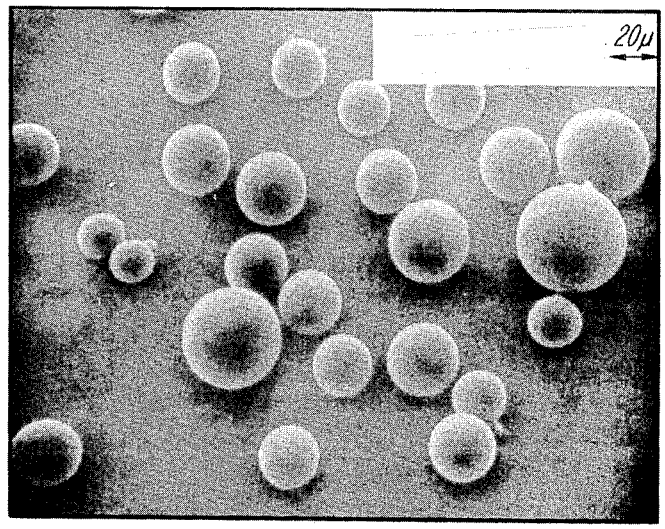
FIGS. 15A and 15B depict gelatin microspheres manufactured by a modified Dilution-Precipitation Method.
Figure 15B:
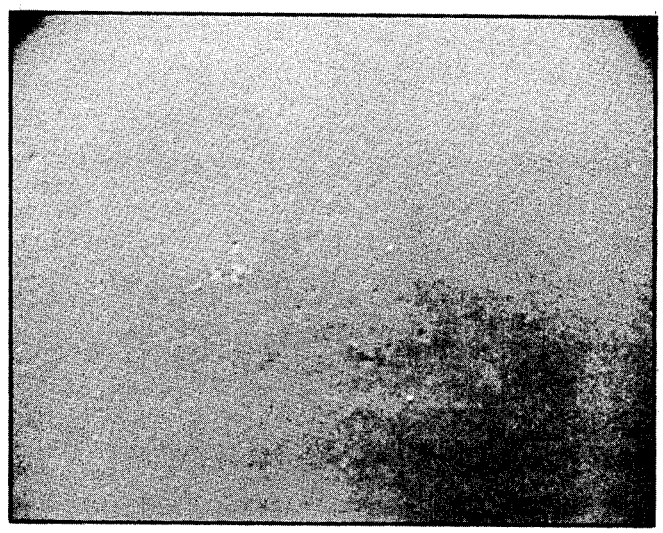

7. The suspension was then filtered through a series of filters to collect the spheres in various size ranges, followed by washing. See FIGS. 15A and 15B for topography of the microspheres.

While the invention has been described and illustrated with reference to certain preferred embodiments thereof, those skilled in the art will appreciate that various changes, modifications and substitutions can be made therein without departing from the spirit of the invention. It is intended, therefore, that the invention be limited only by the scope of the claims which follow.

What is claimed is:

1. A method for preparing a relatively homogenous essentially spherical microporous polymeric network of interconnecting channels containing a pore incorporated agent confined essentially completely inside the channels comprising preparing an agentpolymer-solvent dispersed first phase, dispersing said first phase in a continuous solvent second phase to obtain a suspension, removing solvent from said suspension by freeze drying, or dilution-extraction-precipitation and recovering said microporous polymeric network.

2. The method according to claim 1 wherein said spherical microporous polymeric network is derived from a natural or synthetic copolymer or polymer selected from the group consisting of gelatin, agar, starch, arabinogalactan, albumin, collagen, polyglycolic acid, polylactic acid, glycolide-L(-) lactide poly(ε-caprolactone), poly(ε-caprolactone-CO-lactic acid), poly(ε-caprolactone-CO-glycolic acid), poly(β-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate).

3. The method according to claim 1 wherein said pore incorporated agent comprises a diagnostic or pharmacologically active drug.

4. The method according to claim 1 wherein the solvent in said first phase comprises an inorganic or organic solvent in which said agent-polymer are relatively soluble.

5. The method according to claim 4 wherein said solvent comprises water, hexafluoroisopropanol, methylenechloride, tetrahydrofuran, hexane, benzene, or hexafluoroacetone sesquihydrate.

6. The method according to claim 1 wherein said second solvent comprises a solvent for said continuous phase in which said first phase is emulsifiable.

7. The method according to claim 6 wherein said solvent comprises benzene, dioxane, acetone, methylenechloride, chloroform, carbon tetrachloride, toluene, ethyl alcohol, acetonitrile, p-xylene, tetrahydrofuran, or mixtures thereof.

8. The method according to claim 7 wherein said method further includes the step of employing a diluent-nonsolvent phase to dilute said continuous second solvent phase following dispersion of said agent-polymer solvent dispersed first phase.

9. The method according to claim 1 further including the step of employing a hydrophilic colloidal material to prevent phase inversion.

10. The method according to claim 1 wherein said removal of solvent from said suspension is by dilution-extraction precipitation whereby said dispersed first phase solvent is removed from said agent-polymer.

11. The method according to claim 1 wherein said agent-polymer solvent dispersed first phase is maintained at a temperature ranging between about 10° to 20° C. during said dispersing step.

12. A spherical microporous polymeric network containing a pore incorporated agent therein obtained according to the method of claim 1.

13. A method for preparing a relatively homogenous essentially spherical microporous polymeric network of interconnecting channels containing a pore incorporated agent confined essentially completely inside the channels comprising preparing an agentpolymer-solvent dispersed first phase in which the concentration of said polymer ranges between about 2.5 percent to 18 percent w/w, and said agent-polymer ratio ranges between about 1:1 to 1:10, dispersing said first phase in a continuous solvent second first phase by pressure forcing said first phase through a droplet forming orifice nozzle to obtain a suspension, removing solvent from suspension by freeze drying or dilution-extractionprecipitation, and recovering said microporous polymeric network.

14. The method for preparing a relatively homogenous essentially spherical microporous polymeric network of interconnecting channels containing a pore incorporated agent therein comprising preparing an agent-polymer-solvent dispersed first phase, dispersing said first phase in a continuous solvent second phase to obtain a suspension, removing dispersed first phase solvent from said suspension, and recovering said microporous polymeric network, wherein said removal of solvent from said suspension is by freeze drying of said suspension by a two step freezing procedure to effect separate freezing of first dispersed phase solvent and second continuous phase solvent followed by a two step drying procedure whereby the solvent in both said first and second phases are removed separately allowing recovery of said spherical microporous polymeric network of interconnecting channels.

15. A drug delivery system comprising a spherical microporous polymeric network of interconnecting channels containing a drug wherein said drug is distributed essentially within the channels of said microporous polymeric network.

16. The drug delivery system according to claim 15 wherein said spherical microporous polymeric network is selected from the group consisting of gelatin, agar, starch, arabinogalactan, albumin, collagen, polyglycolic acid, polylactic acid, glycolide-L(-)lactide copolymer poly($\epsilon$-caprolactone), poly($\epsilon$-caprolactone-CO-lactic acid), poly($\epsilon$-caprolactone-CO-glycolic acid), poly($\epsilon$-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisoyanatohexane) and poly(methyl methacrylate).

17. The drug delivery system according to claim 15 or 16 wherein said polymer comprises a polyester polymer of polyglycolic acid or polylactic acid or a copolymer of glycolide and L(-)lactide.

18. The drug delivery system according to claim 17 wherein said polymer is biodegradable.

19. The drug delivery system according to claim 17 wherein said system is suitable for parenteral administration to a human host in need thereof.

20. The drug delivery system according to claim 15 wherein said spherical microporous polymeric network comprises microspheres between about 0.5 to 150 microns in diameter.

21. The microspheres according to claim 20 wherein said diameter ranges between 0.5 to 50 microns.

22. The drug delivery system according to claim 15 wherein said system comprises a sustained release system for the rate controlled release of drug to a specific target site.

23. The drug delivery system according to claim 15 wherein said spherical microporous polymeric network has a degree of porosity of between about 80 to 98 percent as determined by relative void space in relation to the starting concentration of polymer.

24. The drug delivery system according to claim 15 further comprising a coating on said spherical microporous polymeric network capable of promoting targeting of said drug containing microporous polymeric structure to targeted cells or organ systems whereby said drug upon release from said drug delivery system acts predominantly upon the targeted cells or organ systems.

25. The drug delivery system according to claim 24 wherein said coating is comprised of agents selected from the group consisting of proteins, surfactants, antibodies and host receptor site specific drugs.

* * * * *

UNITED STATES PATENT AND TRADEMARK OFFICE
CERTIFICATE OF CORRECTION

PATENT NO. : 4,818,542

DATED : April 4, 1989

INVENTOR(S) : DeLuca et al

It is certified that error appears in the above-identified patent and that said Letters Patent is hereby corrected as shown below:

Column 1, line 50, delete "Glucolic" and kindly insert -- Glycolic --;
Column 3, line 22, after "crystallinity", insert -- (A) --; column 3,
line 24, after "crystallinity", insert -- (B) --; column 8, line 10,
delete "polymeragent" and kindly insert -- polymer-agent --; column 8,
line 50, delete "5-7" and kindly insert -- 5-6 --; column 10, line 25,
delete "5-7" and kindly insert -- 5-6 --; column 12, lines 25-26, delete
"methylenechloride" and kindly insert -- methylene chloride --; column 12,
lines 39-40, delete "polymer solvent" and kindly insert -- polymer-solvent--;
column 12, line 46, delete "extraction precipitation" and kindly insert
-- extraction-precipitation --; and column 12, line 49, delete "polymer
solvent" and kindly insert -- polymer-solvent --.

Signed and Sealed this
Nineteenth Day of December, 1989

*Attest:*

JEFFREY M. SAMUELS

*Attesting Officer*   *Acting Commissioner of Patents and Trademarks*